United States Patent
Vetter et al.

(10) Patent No.: US 10,076,315 B2
(45) Date of Patent: Sep. 18, 2018

(54) SOFT TISSUE BIOPSY OR EXCISIONAL DEVICES AND METHODS

(71) Applicant: TRANSMED7, LLC, Portola Valley, CA (US)

(72) Inventors: James William Vetter, Portola Valley, CA (US); Eugene H Vetter, Portola Valley, CA (US)

(73) Assignee: TransMed7, LLC, Portola Valley, CA (US)

( * ) Notice: Subject to any disclaimer, the term of this patent is extended or adjusted under 35 U.S.C. 154(b) by 0 days.

(21) Appl. No.: 14/852,969

(22) Filed: Sep. 14, 2015

(65) Prior Publication Data

US 2016/0166240 A1   Jun. 16, 2016

Related U.S. Application Data

(60) Provisional application No. 62/052,070, filed on Sep. 18, 2014.

(51) Int. Cl.
| | |
|---|---|
| *A61B 10/02* | (2006.01) |
| *A61B 10/06* | (2006.01) |
| *A61B 17/00* | (2006.01) |

(52) U.S. Cl.
CPC ...... *A61B 10/0266* (2013.01); *A61B 10/0283* (2013.01); *A61B 10/06* (2013.01); *A61B 2010/0208* (2013.01); *A61B 2017/00309* (2013.01)

(58) Field of Classification Search
CPC . A61B 10/0266; A61B 10/0283; A61B 10/06; A61B 2017/00309; A61B 2010/0208
See application file for complete search history.

(56) References Cited

U.S. PATENT DOCUMENTS

| | | |
|---|---|---|
| 5,174,300 A | 12/1992 | Bales et al. |
| 5,251,641 A | 10/1993 | Xavier |
| 5,415,169 A | 5/1995 | Siczek et al. |
| 5,526,822 A | 6/1996 | Burbank |
| 5,873,886 A | 2/1999 | Larsen et al. |
| 5,921,956 A * | 7/1999 | Grinberg ............... A61B 1/0052 600/146 |
| 8,088,081 B2 * | 1/2012 | Field ..................... A61B 10/02 600/567 |

(Continued)

OTHER PUBLICATIONS

International Search Report and Written Opinion in PCT/15/50868, dated Dec. 18, 2015.

(Continued)

*Primary Examiner* — David J McCrosky
(74) *Attorney, Agent, or Firm* — Young Law Firm, P.C.

(57) ABSTRACT

A device for soft tissue biopsy or excision for either hand-held or stereotactic table use may comprise a work element configured to selectively open and close at least one articulable beak configured to penetrate tissue, or follow a central lumen of another device or over a wire in a longitudinal direction. Flush and vacuum tissue transport mechanisms may be incorporated. A single tube or an inner sheath and an outer sheath which may be co-axially disposed relative to a work element may be configured to actuate a beak or beaks and provisions for simultaneous beak closing under rotation may be incorporated.

18 Claims, 14 Drawing Sheets

(56) References Cited

U.S. PATENT DOCUMENTS

| | | |
|---|---|---|
| 2002/0165580 A1 | 11/2002 | Zwiefel et al. |
| 2003/0032955 A1 | 2/2003 | Mulier |
| 2005/0070885 A1 | 3/2005 | Nobis et al. |
| 2005/0209564 A1 | 9/2005 | Bonner et al. |
| 2009/0287114 A1 | 11/2009 | Lee |
| 2010/0121153 A1 | 5/2010 | To |
| 2011/0245725 A1 | 10/2011 | Flatland et al. |
| 2013/0041256 A1 | 2/2013 | Flebig |
| 2013/0096459 A1 | 4/2013 | Vetter |
| 2014/0213932 A1 | 7/2014 | Knoll et al. |

OTHER PUBLICATIONS

USPTO Office Action dated Oct. 16, 2015 in U.S. Appl. No. 14/052,727.
USPTO Office Action dated Oct. 9, 2015 in U.S. Appl. No. 14/853,806.
International Search Report and Written Opinion in PCT/US14/039676, dated Apr. 23, 2015.
International Search Report and Written Opinion in PCT/US14/039688, dated Apr. 23, 2015.
USPTO Office Action dated Oct. 30, 2015 in U.S. Appl. No. 13/903,800.

* cited by examiner

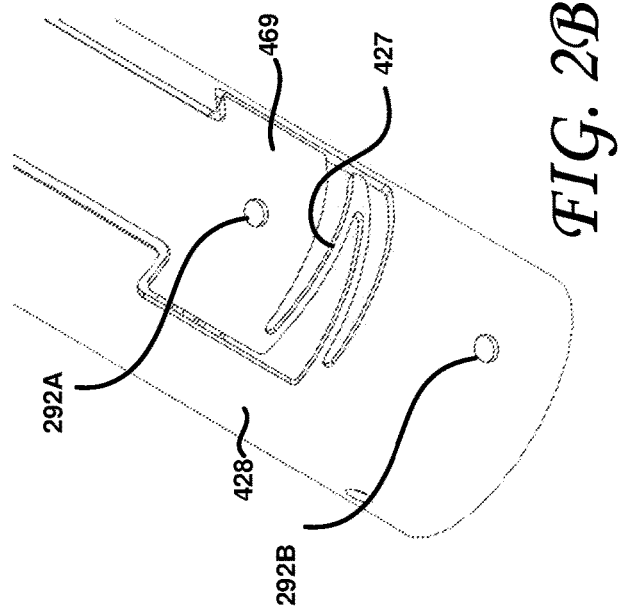
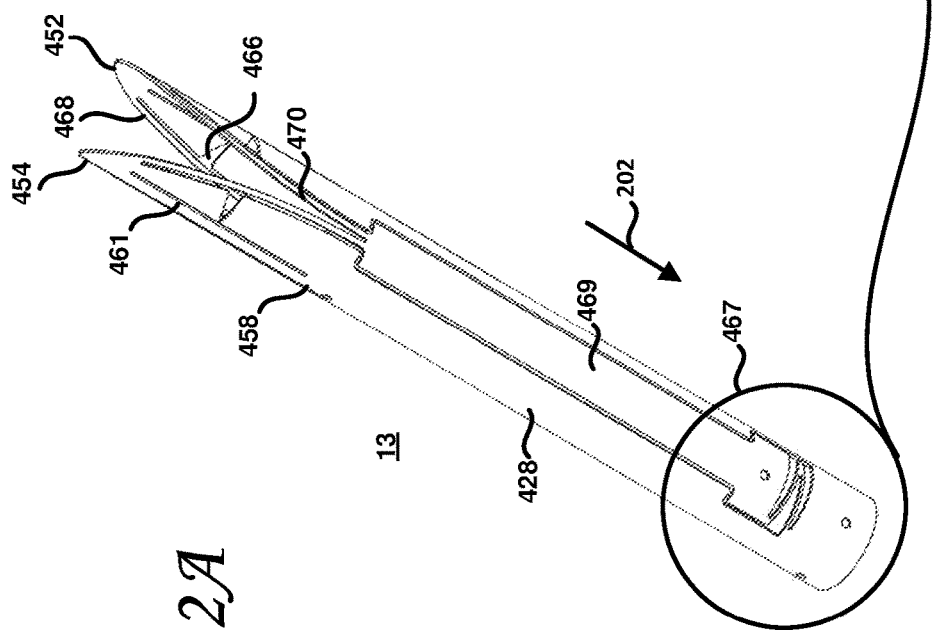

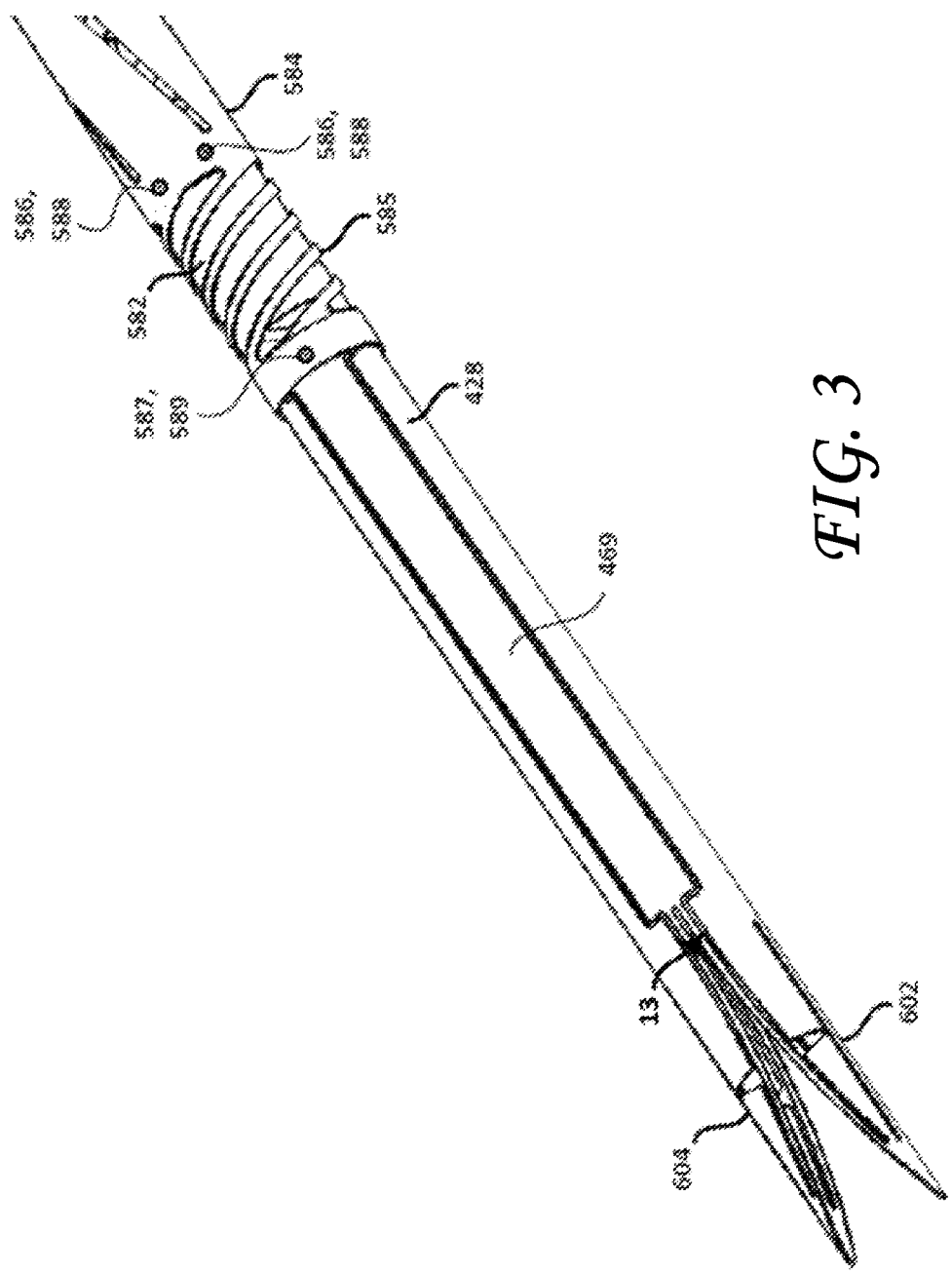

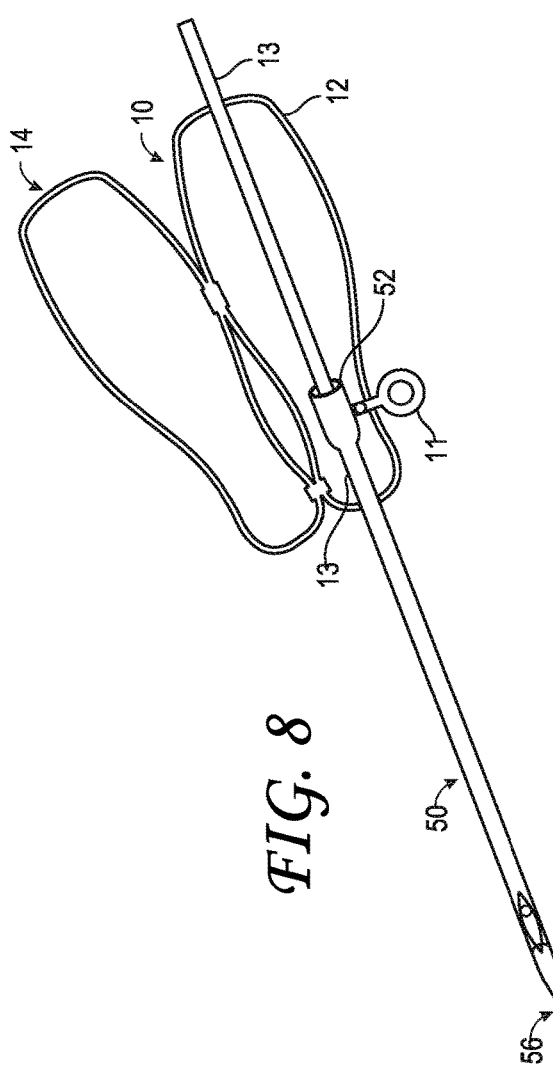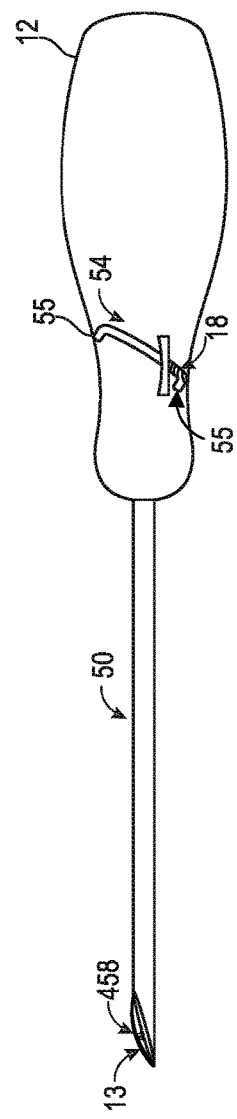

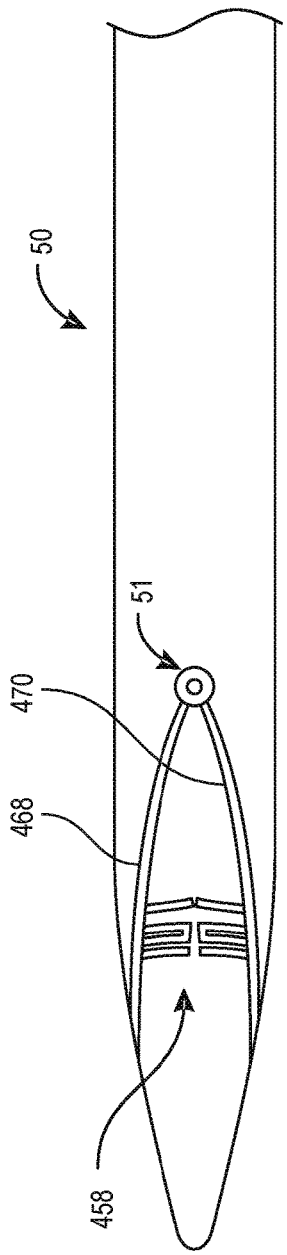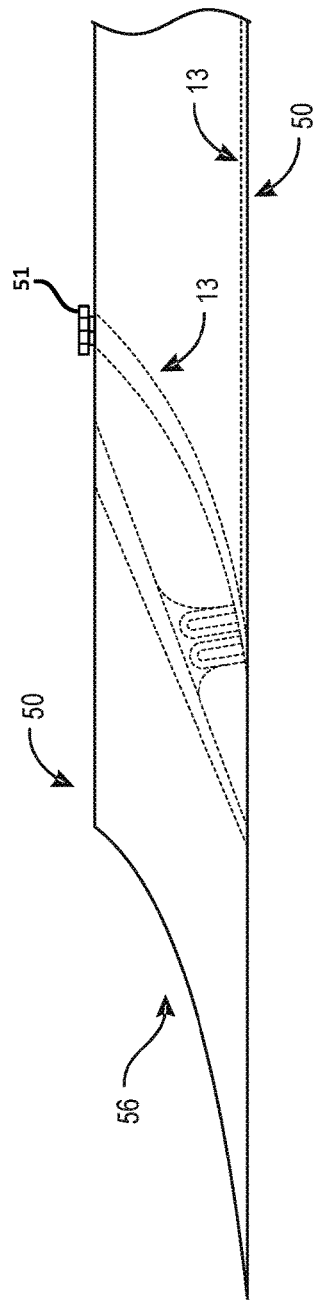

SOFT TISSUE BIOPSY OR EXCISIONAL DEVICES AND METHODS

CROSS-REFERENCE TO RELATED APPLICATIONS

This application claims priority under 35 U.S.C. § 119(e) of Provisional Application No. 62/052,070, filed Sep. 18, 2014, which application is hereby incorporated herein by reference in its entirety.

BACKGROUND

Embodiments relate to medical devices and methods. More particularly, embodiments relate to hand-held or mounted single insertion, single or multiple soft tissue biopsy or excisional devices and corresponding methods for sampling materials such as soft tissue samples. Embodiments further relate to improvements over currently used fine needle aspiration systems, specifically in providing minimally invasive and more reliable aspiration, biopsy or excisional devices and methods.

SUMMARY

Embodiments are drawn to various medical devices and methods that are used for aspiration and soft tissue biopsy procedures. According to one embodiment, a soft tissue aspiration and biopsy device may be configured to remove liquids, semi-solids and single or multiple biopsy samples during a single insertion through the skin (percutaneous procedure) into any soft tissue area of the body. Embodiments may comprise structures and functionality for different phases of a multi-phase biopsy procedure, which may be performed by hand or by device attachment to a stereotactic table stage or Magnetic Resonance Imaging (MRI) stage, including inserting a device through the central lumen of another compatible biopsy device. Embodiments of a soft tissue biopsy device, along with associated related subcomponents described herein, may provide the capability to retrieve solid, contiguous and/or fragmented soft tissues as well as liquid and semi-solid tissues for analysis, diagnosis and treatment and exhibit improvements in functionality and performance relative to present devices and methods for carrying out fine needle aspiration and cavity wall sampling. Embodiments may be configured to be portable, disposable or reusable and may be, for example, electrically-, mechanically-, hydraulically-, pneumatically- and/or manually-powered and operated.

BRIEF DESCRIPTION OF THE DRAWINGS

FIGS. 2A and 2B show details of a work element, according to one embodiment;

FIG. 3 is a view of a twin beak work assembly with an outer sheath attached, according to one embodiment.

FIG. 8 shows a top down view of an excisional device with its lid open, according to one embodiment.

FIG. 9 shows a side view of an alternative handle mechanism of an excisional device with its top closed, according to one embodiment.

FIG. 10 shows a view from the bottom looking upwards of a single beak work assembly of an excisional device according to one embodiment.

FIG. 11 shows a side view of a single beak work assembly in dashed lines inside a trough-shaped portion, both of an excisional device according to one embodiment.

DETAILED DESCRIPTION

Reference will now be made in detail to the construction and operation of implementations of the embodiments illustrated in the accompanying drawings. The following description is only exemplary of the embodiments described and shown herein. The embodiments, therefore, are not limited to these implementations, but may be realized by other implementations. According to embodiments, a device for soft tissue biopsy or tissue excision may be configured to remove tissue, and may have a range of work element diameters ranging from, for example, approximately 21 gauge to 8 gauge, or other appropriate dimensions. According to embodiments, an excisional device may be composed of a single tube or a single tube at least partially disposed within a coaxially-disposed outer tube, which outer tube may comprise a fixed or removable distal trough-shaped portion. The coaxially-disposed outer tube, according to one embodiment, may consist of or comprise one or more coatings. According to one embodiment, the outer tube may be composed of or comprise a stainless steel hypodermic tubing ("hypo tube"). Such a stainless hypo tube, according to one embodiment, may be provided with (e.g., laser) cuts to define a monolithic distal assembly that defines one or more work elements such as beaks, a living hinge that attaches the beak(s) to the generally tubular body of the device or that homogeneously spans between the beak(s) and the generally tubular body of the device. According to one embodiment, cuts in the hypo tube may define one or more tendons configured to actuate the beak(s). The cuts in the hypo tube may also define one or more tendon actuation tabs that enable actuation (e.g., opening and closing) the beak(s) through the tendons and limit the travel thereof. The tendon actuator tab(s) may be located at any location along the length of the hypo tube. According to one embodiment, the tube may be rigid. According to another embodiment, the tube may be flexible over its entire length or one or more portions thereof. The device may also be made of materials other than stainless steel, such as plastics or other suitable materials, which may incorporate the features of the beak(s), tendon(s), and, according to embodiments, tendon actuation tab(s) or an internal tube actuator element.

Figure 1:
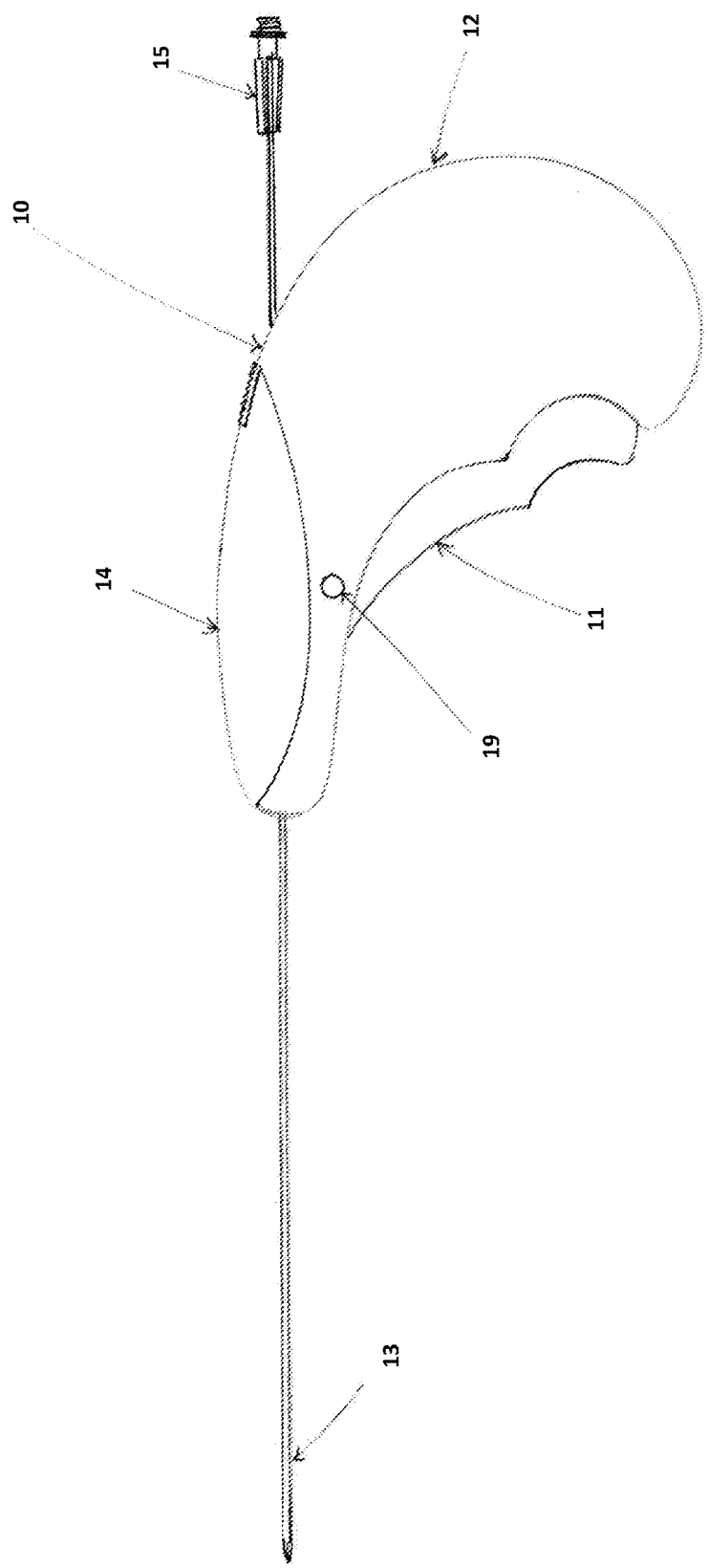
FIG. 1 is a perspective side view of an excisional or soft tissue biopsy device, according to one embodiment.

FIG. 1 shows one embodiment of an excisional device 10. As shown, FIG. 1 shows an actuating lever 11 coupled to a pivot pin 19 that extends through a handle 12, a work element 13, a detachable top cover 14, and a (e.g., luer-type) connection element 15 at the proximal end of the work element, which connection element may be connected to a vacuum or flush or liquid dye system (not shown).

FIGS. 2A and 2B show details of a work element 13, according to one embodiment. As shown in FIG. 2A, the work element may be, according to one embodiment, a monolithic structure formed from a single stainless steel hypo-tube, with laser cuts such as the kerf (created by a laser, for example) shown at 461 to define movable elements such as one or more beaks 452 and 454, a living hinge or hinges 458, a body portion 428, tendons 470 connected to the beaks, and a tendon actuation tab 469. Also shown are cutouts 466 which allow for the beaks to flex inwardly to a closed configuration and outwardly to an open configuration. According to one embodiment, the beaks 452, 454 are biased in the open configuration. From FIGS. 2A and 2B, it can be seen that if a proximally-directed axial force (i.e., in the direction of arrow 202) is applied to the tendon actuation tab 469, the beak or beaks 452, 454 will close by flexion of the living hinge 458 that attaches the beaks 452, 454 to the body portion 428 of the work element 13. The beaks may be sharpened at their distal tips or all along the entirety or a portion of their outer edges such as at 468, including the edges of the tendons 468 and 470, according to one embodiment. It should be noted that according to one embodiment, only one beak and associated living hinge and tendon(s) may be incorporated into the work element 13. In that case, actuation of the tendon actuation tab 469 will cause the single beak to close against an opposing structure such as, for example, an opposite fixed beak or a body portion distal extension such as a trough-shaped portion.

Reference is now made to the proximal end of the work element 13 referenced by numeral 467, another view of which is shown in FIG. 2B. Therein, a body portion 428 of a work element 13 may be mechanically coupled to tendon actuating tab 469 at the proximal end of work element 13. Note that a tendon actuating tab 469, from the embodiment of FIGS. 2A and 2B, is already coupled to a body portion 428 through tendons 468, 470, toward the distal end of a work element 13. That is, an entire work element 13 may be formed of a single homogeneous piece of material—such as from a single hollow tube that is (for example) laser-cut to form the structures shown in FIGS. 2A and 2B. Two beaks are shown. It is to be understood, however, that such need not be the case, as a work element 13 may comprise multiple beaks or a single beak that acts against a non-moveable part, such as a fixed trough-shaped distal portion of a distal sheath or against a fixed, opposing beak that is part of a work element 13 itself.

With continued reference to FIG. 2B, the body portion 428 may be seen, as well as the tendon actuation tab 469. As shown, the proximal portion of work element 13 may comprise a spring or resilient section 427 and positioning holes 292A and 292B. One embodiment comprises a resilient member 427 having one end thereof coupled to a tendon actuating tab 469 and another end thereof coupled to a proximal portion of the work element 13. Such a resilient member 427 may be configured to bias the beak or beaks of a work element 13 in the open configuration, such that a sufficiently great proximally-directed force applied to a tendon actuating tab 469 tends to close the beak or beaks. Conversely, release of such proximally-directed force causes a resilient member 427 to release the energy stored during the compression thereof and return to its less-compressed, thereby exerting a distally-directed force on a tendon actuating tab 469, which causes a beak or beaks to return to its or their default open configuration. Also shown in FIG. 2B, attachment or positioning holes 292A and 292B may be provided on body portion 428 and on tendon actuating tab 469, respectively. Such attachment or positioning holes 292 may, according to one embodiment, indicate the location of, for example, spot welds, as detailed below.

It should be noted that the tendon actuation element or elements 469 may be located at the extreme proximal end of the tube, which may be of any suitable length, such as, for example only, anywhere from 4 to 8 inches in length. According to embodiments, the work element 13 may be coated with an exterior coating, or may be placed into an external tube, which may serve to actuate the tendon actuation tab as described further herein.

The shape of sharp cutting elements or beaks in work element 13, such as the embodiment thereof shown in FIGS. 2A and 2B, for example, provides substantial support vectors for all movements required of such cutting blades during rotation, opening/closing and axial motions (not shown). Using the nomenclature of FIG. 1 in particular, this embodiment enables sharp cutting elements of beak or work element 13 to be made extremely thin, which fulfills a requirement that for any given outer radial dimension of a tubular coring structure, including a cutting beak assembly (see also FIG. 1), the caliber of the core sample retrieved from the patient should be as large as possible. The shape(s) of sharp cutting elements of beak work element 13 specified for use in coring and part-off, according to embodiments, enable the device 10 to obtain a full diameter (with respect to the diameter of the work element 13, for example) core sample, and in fact larger than full diameter, which may be desirable in order to compress, "stuff", or pack in as much tissue sample as possible into a tubular coring assembly. Coring of a larger than full diameter tissue sample may prove advantageous from diagnostic and clinical standpoints, by providing more sample (not shown) for analysis or by removing as much of the target tissue as possible during a single excision.

According to one embodiment, articulable beak(s) may be generally described as being or comprising one or more hyperbolic segments of one or more sections of a hollow cylinder, such as a hypo tube. Variations including complex curves may be incorporated into the shape of articulable beak(s), to optimize function in different sections of the edges of articulable beaks. Moreover, first and second articulable beaks, according to embodiments, may have slightly different shapes from one another. The angle formed by the distal portion of first and second articulable beaks may be, for example, from about 5 to 50 degrees, with the relative term "about" corresponding to 10%, for example. According to one embodiment, the angle may be between about 10 and 30 degrees. According to another embodiment, the angle formed by the distal portion of first and second articulable beaks may be about 18 degrees.

Note that, according to one embodiment, an entire work element, including first, or first and second (or multiple) articulable beaks 452 and 454, along with their first and second tendons, beak actuation mechanism 469, living hinges 458 (as shown in FIG. 2A) connecting first and second articulable beaks to a body portion of a work element, and travel limiter structures may together be a single monolithic structure formed of a same material that may be (e.g., laser-) cut from, for example, a single solid hypo tube. That is, these structures may be formed together of a same piece of unbroken homogeneous material.

FIG. 3 is a view of a two beak work assembly, according to embodiments. FIG. 3 shows components of a work element 13 (comprising, e.g., body portion 428, one of the tendon actuation elements or tabs 469 and first and second articulable beaks 602, 604. The work element 13 may be mechanically coupled to a proximal sheath 584 as an extension of the tubular structure. As suggested at 586, 588 and at 587, 589, a proximal sheath 584 may be spot-welded to the work element 13 in such a manner as to enable differential motion of the body portion 428 of the work element 13 relative to the tendon actuating tabs 469 thereof when the helical element 585 compresses and extends, which differential motion actuates (e.g., opens and closes) first and second articulable beaks 602, 604. Significantly, the attachment of the proximal sheath 584 to both the body portion 428 and to tendon actuating tabs 469 of the work element 13 results in substantially equal torque being imposed on the constituent elements of a work element under rotation, thereby maintaining the structural integrity of the work element 13 as it is used and as first and second articulable beaks 602, 604 cut through variably dense, fibrous and/or vascularized tissues.

Figure 4:
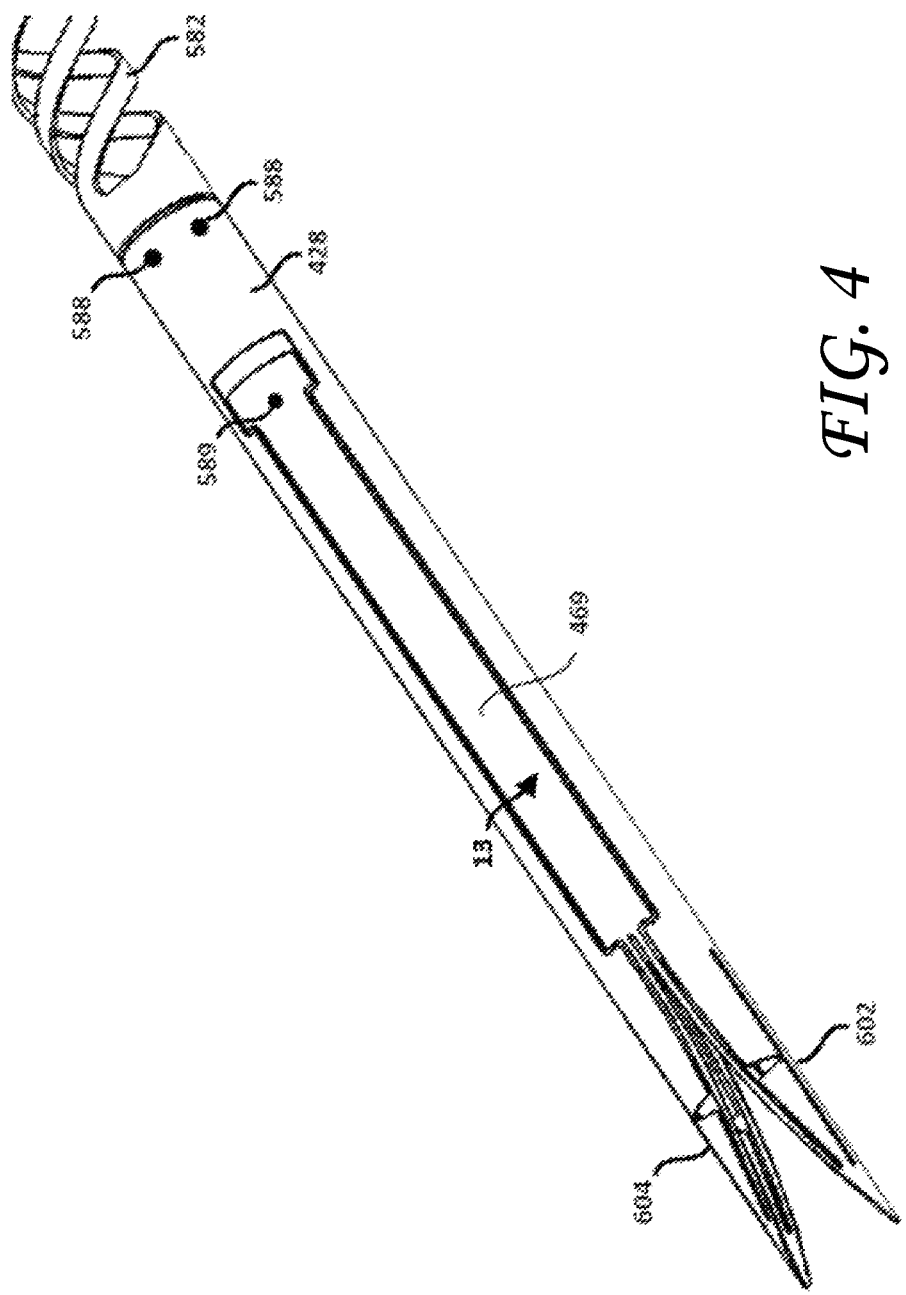
FIG. 4 is a view of a twin beak work assembly with an attached and elongated flexible body portion extension, according to one embodiment.

FIG. 4 is a view of a work element 13 comprising a multiple beak 602, 604 assembly, according to one embodiment. FIG. 4 shows a body portion 428, tendon actuation element 469 and first and second articulable beaks 602, 604 of a work element 13, together with an attached flexible extension element 582, which may simply be an elongation of the body portion 428 and continuous with regard to its structure. An outer sheath, if desired, may be added but is not visible in this view. As shown, a flexible extension element 582 may be co-axially disposed relative to the body portion 428 of work element 13 and may be of the same or substantially the same diameter. As noted above, the work element 13 and the extension element 582 may be formed of, or cut from, a single piece of material such as, for example, a stainless steel hypo tube. According to another embodiment, the flexible extension element 582 may be of a different diameter than the body portion 428.

One embodiment of the present material delivery or removal device 10, as shown in the figures, may be implemented in a hand-held configuration comprising an ergonomically comfortable and secure handle 12 (as shown in FIG. 1) at its proximal end. Work element 13 may extend from the handle 12 so that the material delivery or removal device 10 may be easily grasped, directed and operated with one hand while the other hand is free to hold a guiding probe such as an ultrasound transducer. However, it is to be understood that embodiments may readily be configured to fit onto any number of guiding devices such as a stereotactic imaging stage or other guidance modality such as MRI (not shown). As shown, one embodiment of the material delivery or removal device 10 may comprise one or more sharp elements 13 (herein, alternatively and collectively referred to as "work element", "beak", "beak assembly" or "beak element" or "beak elements") projecting forward distally from the handle 12 for the purpose of forward penetration, coring and parting off of cored tissue in a simple forward motion procedure. As shown, one embodiment may comprise a distally-disposed beak work element 13 that may comprise one or more sharp cutting tip blades to penetrate to the target site of the intended excision. The ability of the present material delivery or removal device 10 to repeatedly retrieve multiple materials during a single insertion may be augmented with an external vacuum source (not shown). The entire device 10 may be configured to be disposable or may be configured to be reusable in whole or in part.

According to one embodiment, a method of carrying out a biopsy or excisional procedure may be preceded by procedures including, for example, imaging the tissue of the organ or structure of interest and identifying the target lesion(s) or tissue to be biopsied or excised. The skin may then be cleansed using sterile techniques, and the patient may be draped and anesthetics may be delivered. The distal tip of the present device 10 may then be introduced through a skin nick incision. According to one embodiment, a guiding element may be provided coaxial with, in tandem with or adjacent to the long axis of elements of the device, such as the work element 13. Alternatively, the guiding element may be a completely separate or separable entity, such as a removable outer sheath, with or without a trough-shaped distal portion that may function as a locating tube. Such a locating tube may be pre-placed by an operator skilled in imaging and targeting and fixed in place near or within the target tissue. After placement and fixation, an operator may then proceed by advancing the device 10 over a previously precisely placed and anchored guiding element to the target tissue site. Tissue penetration to the target site may be carried out with the work element 13 in an open or closed configuration (that is, the beak or beaks may be open or closed), which may be selected by the operator. Since the device 10, according to one embodiments, may be provided with aspiration through its central lumen, the proximally directed force generated by such suction will tend to draw cored tissue into the aforementioned central lumen, and may further allow the tissue to be collected at the proximal end of the device 10 after the beak(s) have closed and parted off the tissue.

The device 10 may be advanced percutaneously to the target tissue site and fluids or anesthetics may be delivered through the central lumen thereof during that process. An optional delivery stage may also be initiated, to deliver, for example, the contents of a preloaded cartridge comprising tracer elements like visible dyes, echo-enhancing materials and/or radioactive brachytherapy or tracer elements, or others, for example. Medications such as epinephrine or anesthetics which may be delivered at any stage of the procedure either directly through open beaks, through the living hinges of closed beaks or via a reverse flow from a flush system built into the device, according to embodiments. Tissue samples or excised tissue may then be taken. The cutting beak assembly of embodiments of the devices may be used, without alteration of their shape, attachment or any other modification, to penetrate tissue on approach to a target lesion or site. The one or more articulable beaks of work element 13 may then be used to open and core the tissue specimen, and to thereafter part-off the specimen at the end of the coring stage. The parted-off pieces of tissue may be collected in the central lumen of the device. Vacuum may be used for tissue and fluid aspiration through a connection at the proximal end of the device, as shown in FIG. 1. Fluid flushes containing material from the tissue site may be collected by aspiration to be discarded or saved for later cytological analysis.

It is to be understood that the above description is but one exemplary methodology and that one or more of the steps described above may be omitted, while other steps may be added thereto, depending on the target site within the body or other operator methodologies. The order of some of the steps may be changed, according to the procedure.

Figure 5:
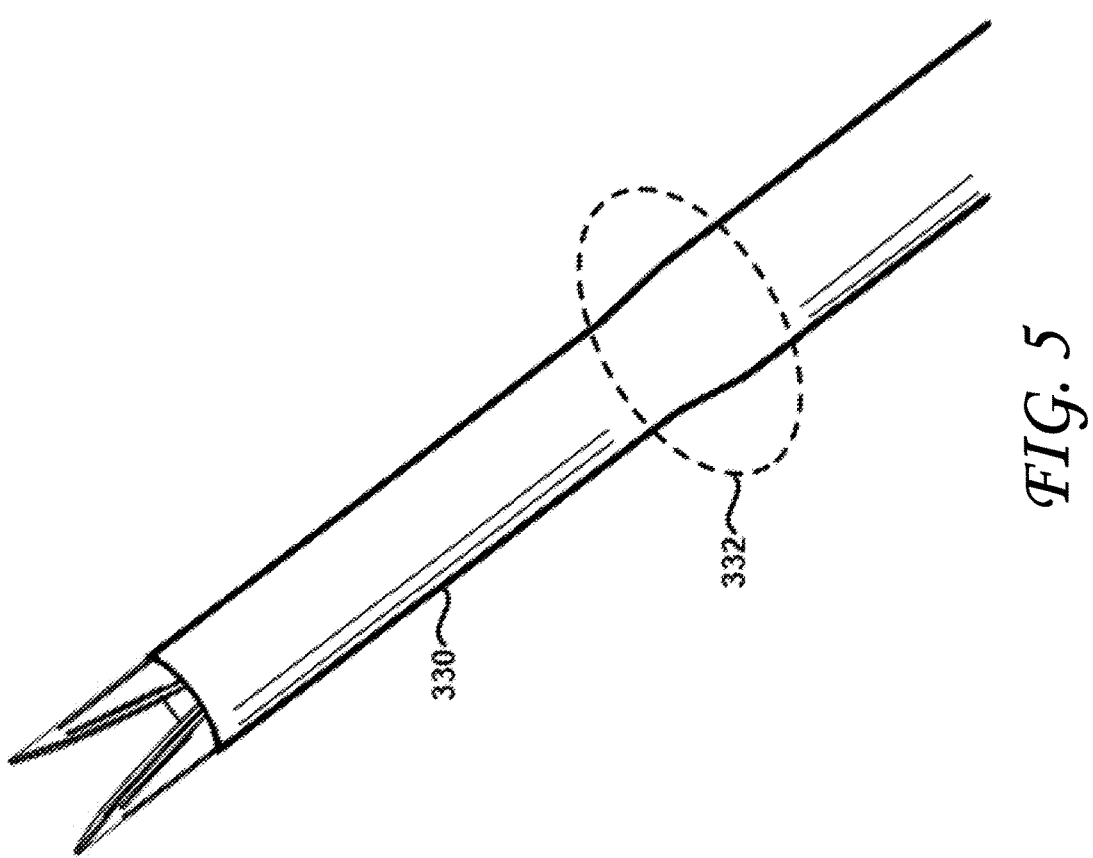
FIG. 5 shows a monolithic beak assembly of an excisional device comprising an outer sheath, according to one embodiment.

FIG. 5 shows one embodiment of the present excisional device's work assembly. In FIG. 5, an outer sheath 330 has been fitted over an assembly comprising a monolithic beak work element 13. For example, an outer sheath 330 may comprise polyimide or may comprise or be formed of stainless steel. An outer sheath 330 may further be configured to be removable and may incorporate features such as an elongated trough-shaped extremity. An outer sheath 330 may extend distally to beaks of a monolithic beak work element 13, may expose a greater proportion of a monolithic beak work element 13 or may cover a significant portion of beaks, which may be controlled during use, according to embodiments. In one embodiment, a simple collar attached to the tendon actuation tab of the work element may be acted upon by the shoulder element 332 of the outer tube to actuate the beak or beaks, or may act upon the increased outer diameter of the proximal sheath of FIG. 3, for example.

According to one embodiment, an entire assembly of split tube, beak, living hinge and tendons may be formed of a single tube that may be, for example, laser cut (not shown, but easily envisioned wherein the lower half, for example, continues to become the body portion of a beak assembly and the upper half of the split tube continues to become a tendon actuating member, or vice versa).

Flush and liquid/solid materials delivery mechanisms may be incorporated into the device 10, according to embodiments, to aid in tissue transport to, for example, a transfer magazine, flush collection bag or bottle (not shown). A suitable transfer magazine and other structures are disclosed in co-pending and commonly assigned U.S. patent application Ser. No. 14/050,771 entitled "SOFT TISSUE CORING BIOSPY DEVICES AND METHODS", the entire disclosure of which is hereby incorporated herein in its entirety. Flush fluids and other materials may also be delivered to the tissue site through the central lumen of the device 10, with beak(s) in the closed configuration (as described for liquids under FIG. 2A above through living hinge slots) or in the open configuration, according to embodiments. As previously described, fluids, solids and other materials may be delivered to the tissue site through the central lumen of the device 10, and various slots and mechanisms such as the open beak(s) may be used in conjunction with flush fluids to gather and transport cells and liquids from the tissue site for later cytological analysis.

Figure 6:
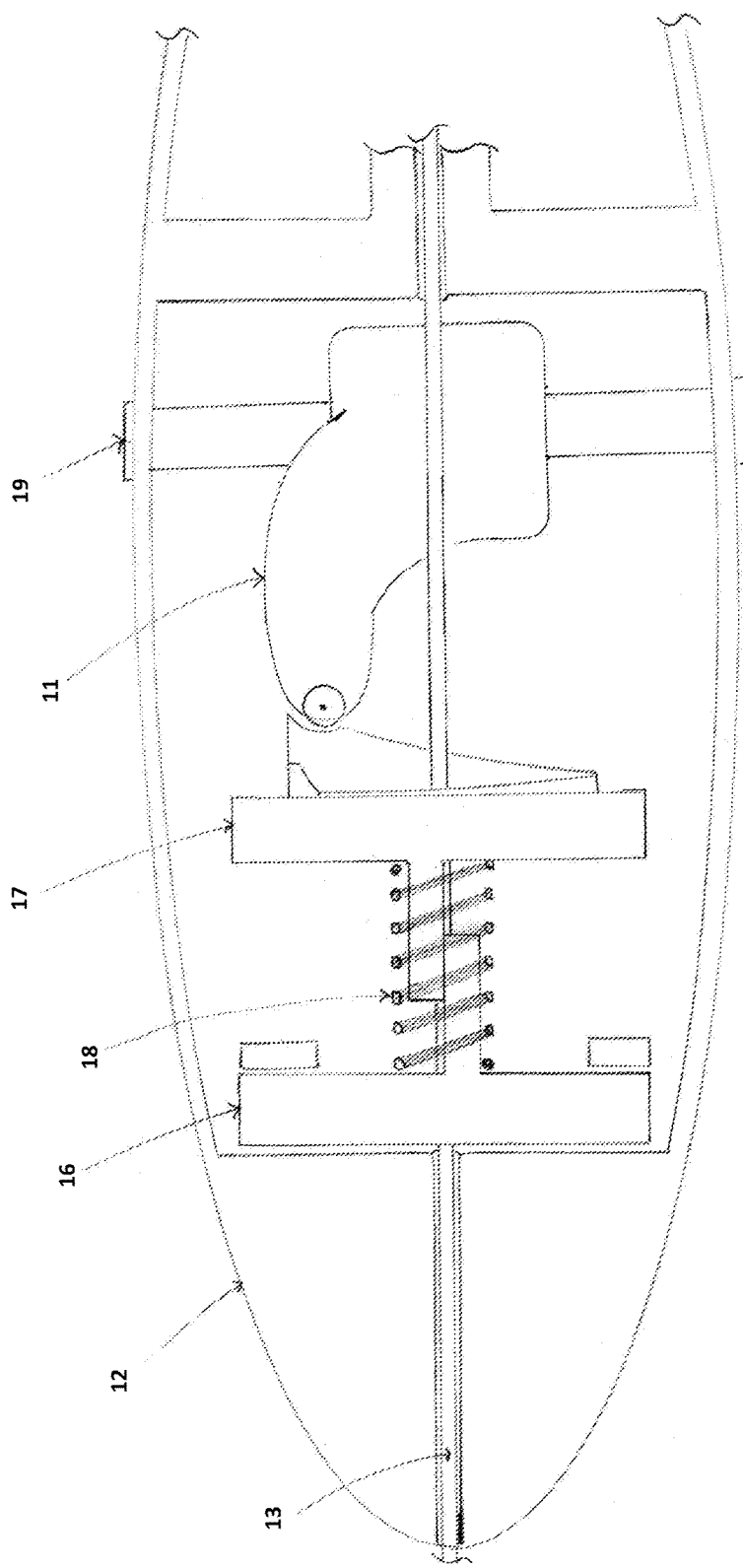
FIG. 6 shows a top-down perspective view of various details of an actuation mechanism inside the handle of an excisional device, according to one embodiment.

FIG. 6 illustrates a top view of device 10, with its top 14 removed to show the inner structures thereof, according to one embodiment. As shown, FIG. 6 shows the work element 13 lying in a semi-circular trough within the handle 12. According to one embodiment, the handle 12 may be configured such as to allow drop-in replaceable work elements or assemblies 13 through the open top of handle 12, according to embodiments. Also shown in this figure are two circular dogs, one of which, dog element 16, acts as a thrust bearing, allowing rotation. Dog element 16, in the implementation shown in FIG. 6, is connected to the tendon actuation tab 469 of the work element 10 if the work element is a single tube (as shown in FIG. 2A), or on the outer tube (which if present may act on the tendon actuation tab where the work element is composed of an inner and outer tube, according to embodiments). This dog element 16 is constrained from moving axially distally or proximally by bulkheads fore and aft in the body of the handle 12 and may contain an O ring or other sealing mechanism against the outside circumference of the inner tube assembly, according to one embodiment. The thrust bearings or dogs 16 and 17 may be fixed to their respective elements of the work element 13 by adhesive or other appropriate fixation mechanism. Dog element 17 serves as a thrust bearing allowing rotational and axial movement and is attached either to the body portion of the work element 13 in a single tube work element embodiment, or to the inner tube of the work element, if present, according to embodiments. It should be noted that each of the dog elements 16, 17 comprises an extended half shaft of semi-circular or other form that work in concert to ensure that any rotation of the thrust bearings is coordinated while allowing axial motion, one relative to the other. The full travel from extended position to fully closed axial position of the two half shafts define the distance necessary to move the tendon actuation tab 469 to open and close the beaks 452, 454 or 602, 604, including an over center opening position or an over center closed position, according to one embodiment. Thus, a distally-directed thrusting force of the top extension of the lever 11 rotating on its pin 19 will cause the beaks 452, 454 or 602, 604 to close, and relaxing that force will allow the beaks to open, aided by spring ore resilient element 18 between the dog elements 16 and 17, according to one embodiment. According to another embodiment, spring element 18 may not be present or may be replaced by a flexible coating between the dog element half shafts, and the force opening the beaks may be realized as a result of the resilient member 427 shown in FIG. 2B. In one embodiment, application of a suction force at the proximal end of the device may be sufficient to close the beaks 452, 454 or 602, 604 at the distal end of work element 13. Such force may be easily envisioned by attaching a syringe, for example, to the Luer connection 15 at the proximal end of the device shown in FIG. 1. Further, if a system of two one-way valves are incorporated into a (closed-chamber type) syringe/valve combination suction device, action on the syringe in either direction will serve to increase and maintain vacuum in the central lumen of the device, according to one embodiment. Furthermore, actuating lever 11 of FIG. 7 or some other control may be used to selectively apply the suction force to cause the one or more beaks of the work element to flex and assume their open or closed configurations. In such an embodiment, application of the suction force may cause the one or more beaks to assume the closed configuration, whereas reducing or shutting off the vacuum causes the suction force to decrease, thereby causing the beak or beaks to assume their open configuration.

In certain clinical situations, it may be desirable to introduce a solvent into an area (may be simply water or saline for example, or may incorporate agents that provide local anesthetic or bleeding control agents or others) such that cells, tissue and thick, viscous liquids or semi-solids may be bathed in such a solvent in order to facilitate transport. In such a situation, it may be desirable to aspirate simultaneously with introduction of fluids for this purpose. In conjunction with the working elements of embodiments of a device described herein, a closed-chamber type syringe may be equipped with suitable valve and tubing elements to permit single plunger action to perform both functions simultaneously. This may also be accomplished with dual plunger, single syringe equipment for example (not shown).

In addition to directly providing a distally-directed axial force to actuate the beak(s) 452, 454 or 602, 604 of work element or assembly 13, the circular dog element 17's rear face may have a circular ramp incorporated, according to embodiments. As shown in this figure, the forward facing tip of the actuating lever 11 may comprise a roller, which engages the circular ramp. In this embodiment, forward axial pressure exerted on the circular dog 17 not only serves to close the beak(s) of work element 13, but also imparts a simultaneous twist action or motion on the work element 13, amounting to, in this illustration, nearly one full revolution. The ramp feature may be extended or restricted to allow more or less revolutions before, during and even after the beak closing action, which may be accomplished by varying such elements interaction as those associated with the spring strength, length of the dog half shafts (which define the full range of beak opening and closing travel desired), length and pitch of the circular ramp, and number of turns on the circular ramp, according to embodiments. This twisting action or motion imparted to the work element 13 during beak closing may aid in parting off tissue to be excised. It should be noted that when pressure from lever 11 is relaxed, the circular ramp of dog element 17 will again rotate in the opposite direction simultaneously with beak opening of work element 13. According to one embodiment, dog element 17 may incorporate a wind-up type spring to aid in counter-rotation back to the dog 17's home position. A simple sliding lock mechanism may be used to prevent rotation of dog element 17. Alternatively, a simple friction brake mechanism may be provided to retard the rotation of the work element 13 to match a desired forward axial movement to rotation degree ratio, according to one embodiment. According to a further embodiment dog element 17 may extend externally through the handle 12, which allows an operator to manually twist the work element, or open and close the beaks of the work element, which may aid in penetration, coring or parting off of difficult (e.g., dense fibrous) tissue. Alternatively, an operator may simply rotate the dog element 17 counterclockwise so that the actuating lever 11 rests in its farthest distal point on the circular ramp, and in that mode, beak actuation may be performed without any concurrent twisting motion.

According one embodiment, the dog elements may comprise of collars attached to body portion and tendon actuation tabs/outer tube. In such an embodiment, no provision is made for twisting as beak opening or closing occurs. In this implementation, the operator's fingers may actuate the dog elements 16, 17 manually, providing relative axial movement between the two, or a simple scissors-action type clamp may actuate the collars to open or close the beaks as desired. Another embodiment may feature a tubular shaped handle 12, with a simple protrusion to operate the proximal dog or collar to actuate the beak(s), and such a mechanism may also include a provision for a circular ramp or other mechanism to impart a twisting motion during beak actuation. A sliding lock may also be provided to enable the beaks of the work element 13 to be locked in an open or closed position, as desired. Additionally, work element 13 may be configured with various external features, such as a spiral pattern to aid in tissue penetration. Similarly, the inner lumen of the work element 13 and/or other lumens through which cut tissue travels, may be provided with surface features or rifling, to aid in tissue transport in the proximal direction (i.e., towards the operator). Tissue penetration to a target sample site may be in either beak(s) open or beak(s) closed mode, at the operator's discretion.

Figure 7:
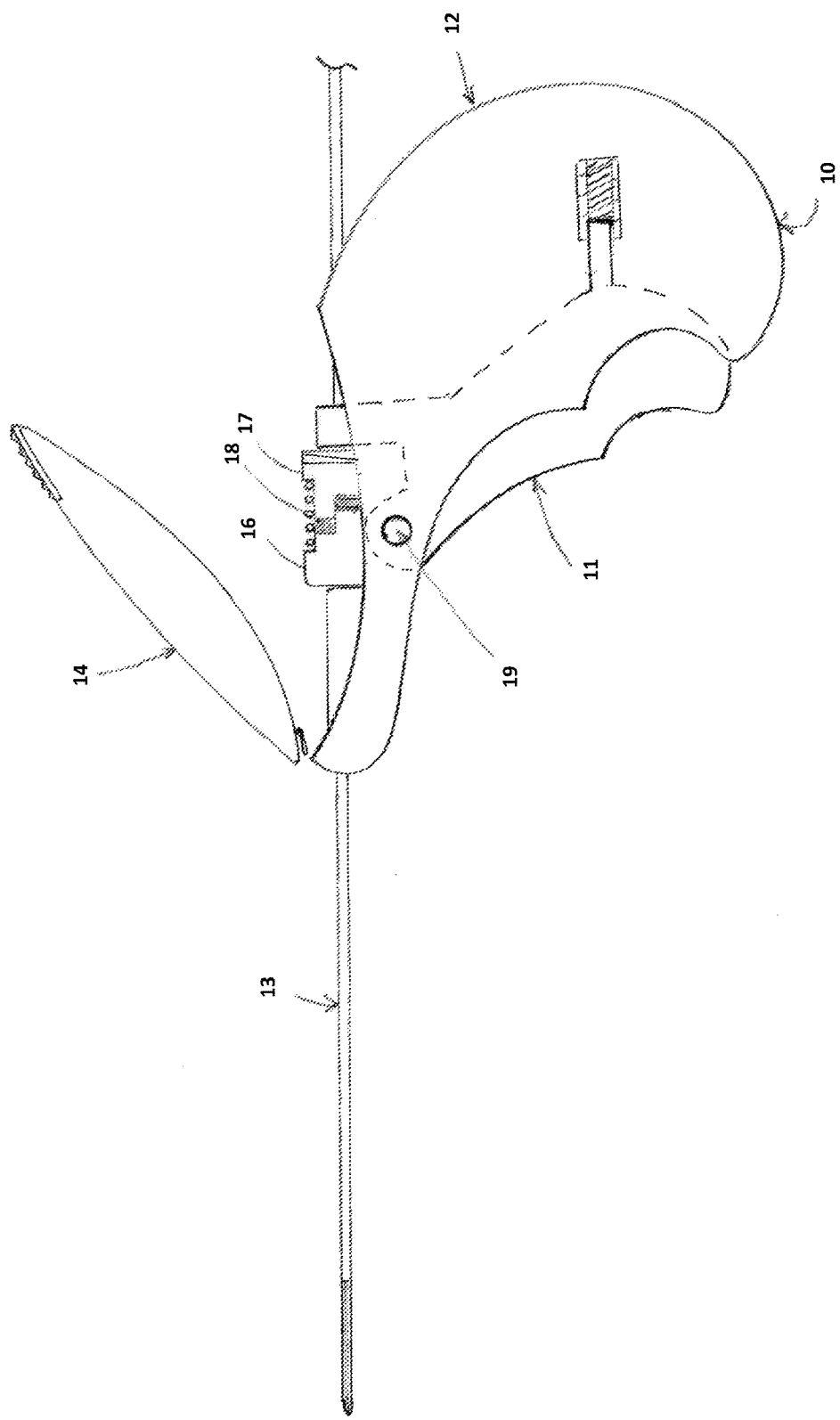
FIG. 7 shows a perspective view of an excisional device with its top unlatched, according to one embodiment.

FIG. 7 is a side view of a biopsy device 10, according to one embodiment. In this view, the lever 11 may be seen in internal profile (by the dashed lines) with its pivot pin 19 and return spring, and the work element 13 with its dog elements 16 and 17 and spring element 18. The top or cap element 14 with its latch mechanism has been displaced to illustrate the ease of dropping in replaceable parts (including, for example, work element 13, actuation mechanism 16, 17 and 18 and/or any of the structures described relative to FIG. 6) to the reusable handle 12 as desired by an operator. With the cap element 14 removed, a work element with its corresponding dog elements 16, 17 may be simply dropped into place and the top or cap element 14 may be replaced.

FIG. 8 illustrates a perspective view of an open-top device 10 according to one embodiment. As shown, the device 10 may comprise work element 13 lying in a semi-circular trough within the handle 12 as well as trough-shaped portion outer sheath 50 53 fixed with respect to rotation and axial or longitudinal translation to handle 12. It should be noted that the removable cover or 14 of FIG. 1 has been opened sideways, and that the handle contains provisions to drop in replaceable work elements or assemblies 13 through the open top of handle 12. The embodiment shown in FIG. 8 comprises a mechanism that is activated by pressing downwards on a thumb slide 11, which rotates an inner beak or beaks work assembly 13, causing it to also translate forwards (distally, away from the operator) and to occlude completely with and close down upon the outer sheath trough-shaped portion 50. The outer sheath trough-shaped portion 50 is fixed to handle 12 to a degree sufficient such that it neither translates nor rotates. Shown in subsequent figures is a slot 53 in the trough-shaped portion sheath 50 that enables the inner working beak assembly of work element 13 to rotate while translating forwards and backwards, carrying itself in those directions simultaneous with rotation, and, at the most distal end of its translation, to close down and occlude against the distal portion of the trough-shaped portion 50, causing a parting off of any tissue or substances that remain attached to the host material.

FIG. 9 shows a side view of the device 10 of FIG. 8. Indeed, FIG. 9 shows thumb slide 11 nearly at the end of its travel, compressing return spring 18 nearly fully. Also shown is a locking slot extension 55 at the bottom of the slot as well as at the top of the slot. When the thumb slide 11 is at the top of the slot in this view, the working single beak of work element 13 is retracted to the proximal opening of the trough-shaped portion element 50 and the single beak of work element 13 with its living hinge and tendons is nested at the bottom inner surface of the trough-shaped portion 50, providing maximum streamlining and minimum frontal area as the device is advanced into hard, soft or cystic tissues. Once in the desired location, pressing down on thumb slide 11 forces, via its attachment collar 52, the single beak of work element 13 to translate forward the length of the trough-shaped portion 50 opening 56 while rotating, and upon reaching the distal tip, forward excursion of the tendon bases are slowed by the slot 53 in the trough-shaped portion (shown in detail in later illustrations), while rotation is allowed to continue until a point where simultaneous forward excursion and rotation are stopped as determined by the geometry of the slot 53 in the trough-shaped portion. The combination of forward excursion of the tendons slowing as determined by rivet 51 following slot 53 pathway geometry during continued rotation of the entire inner tube/working beak assembly, followed by both excursion and rotation coming to a complete halt at the termination of slot 53 simultaneous with or just after simultaneously to exert increased pressure against trough-shaped portion 50's surface(s)/edge(s) with, complete occlusion of the single beak edges with the trough-shaped portion inner surface/edge, completes the cycle of rotation, forward excursion and parting-off. Significantly, this embodiment enables, for a same minimized diameter, a larger opening due to the longitudinal opening area being added to the cross-sectional area through which sticky fluids, semi-solids and solids may travel, taking advantage of an increase in length of the opening 56 as opposed to simply increasing diameter, to increase the total opening area.

Figure 12:
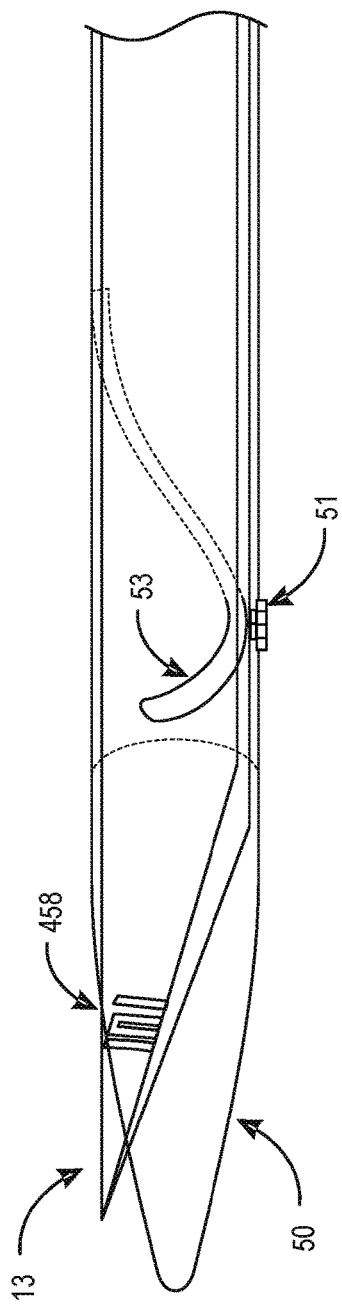
FIG. 12 shows a view from the bottom looking upwards at a trough-shaped portion with a single beak working element partially rotated (in side view, dashed lines) within a trough-shaped portion element both of an excisional device according to one embodiment.
Figure 13:
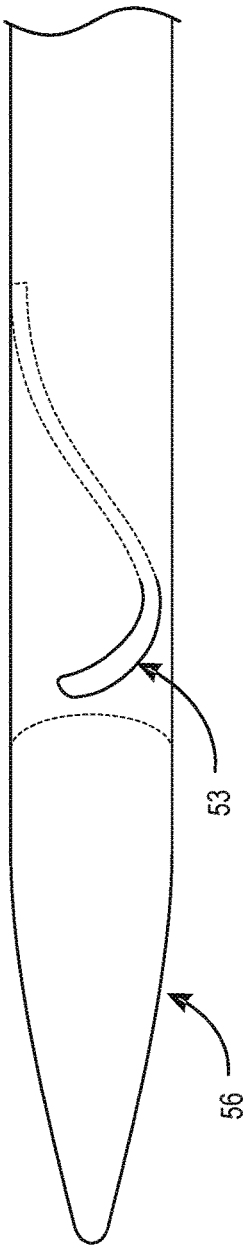
FIG. 13 shows a view from the bottom looking up of a trough-shaped portion of an excisional device with its activation slot partially dashed to indicate its position on the top side of a trough-shaped portion of an excisional device according to one embodiment.

FIG. 10 shows details of components configured to enable the functionality described above relative to FIGS. 8 and 9. As shown, the single beak working element with its tendons 468, may be attached to a button rivet 51 that rides in the slot 53 formed in the wall of the trough-shaped portion 50, as shown in FIG. 11. Forcing the rivet to ride in the slot 53 in the trough-shaped portion entrains the working element 13 in both rotation and distally-directed translation. The geometry of the slot may be configured to hold the tendons back in forward excursion at a point just before the working element reaches the distal end of the trough-shaped portion. Both the tendons and the rest of the tube including the backbone/living hinge elements stop their rotation at the same time at the point where flexing of the living hinge backbone enables the single beak to rest firmly against the trough-shaped portion. Moving the rivet head 51 back along the curved spiral slot in the trough-shaped portion resets the beak assembly of work element 13 open, retracted and rotated back again to nest against the inner wall of the trough-shaped portion 50, aligned with its inner wall. FIG. 11 shows the inner beak in this nested position, while FIG. 12 shows the working beak element about halfway around its rotation cycle as well as just over halfway along its distal translation. FIG. 13 shows the trough-shaped portion element by itself for clarity, the proximal extent of its typical opening 56 indicated by way of example, by a dashed line just ahead of the spiral activation groove.

Figure 14:
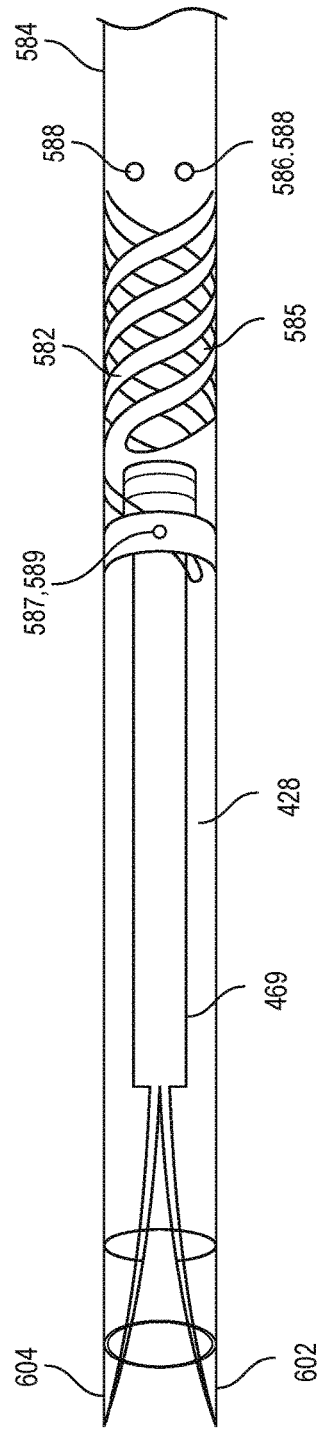
FIG. 14 is a view of a twin beak work assembly with an outer sheath attached, according to one embodiment.
Figure 15:
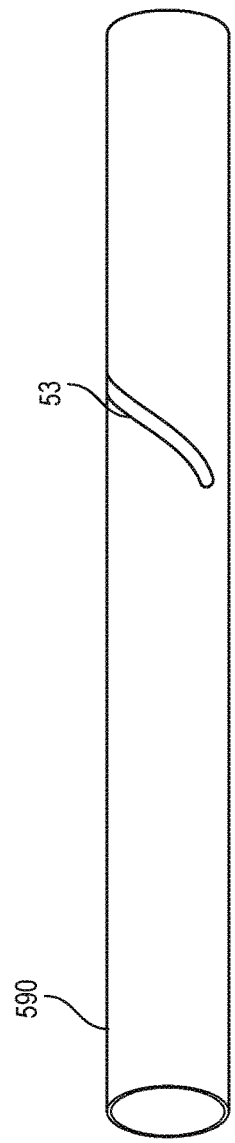
FIG. 15 is a view of an outer sheath with its activation slot shown according to one embodiment.
Figure 16:
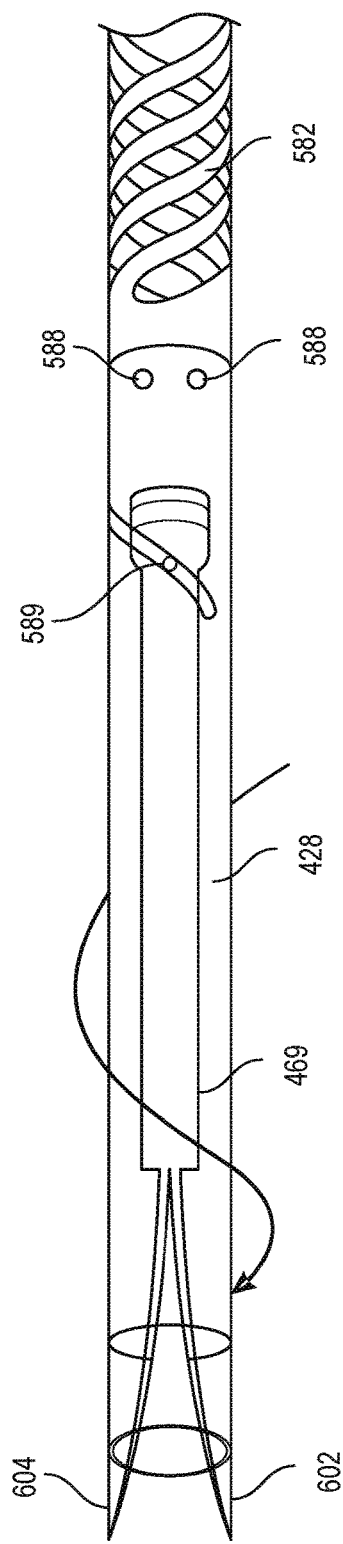
FIG. 16 shows a monolithic beak assembly of an excisional device with an outer sheath over it, in two positions, according to one embodiment.

FIG. 14 shows all the elements described previously as in FIG. 3, included again here for reference. FIG. 15 shows an outer sheath tube 590 with a set of activation slots 53 similar to the single slot 53 described in reference to FIG. 13. The second slot is not shown in these illustrations for simplicity. FIG. 15 shows one embodiment in which the distal end of outer tube 590 is a sharpened rim rather than a trough-shaped portion, for the purposes of interacting most optimally with more than a single beak in the work assembly 13. Otherwise, the slot elements perform the same function in that they determine the translation extent of elements 469 as well as the rotation extent of the working beaks assembly, including 469, 602, 604 and 428 for example. The slots in the outer sheath tube then, allow unsheathing of the beak elements for the purposes of severing any tissue that may remain attached to its host matrix. The handle shown in FIG. 8 and FIG. 9 may be the same for the multi-beak working element as for the trough-shaped portion/single beak tube components, enabling both working tube element configurations to be used with the same handle. In one embodiment, tube sets can be packaged together with trigger/collar assembly 11 and simply dropped into handle 12, which may be reusable or disposable.

Figure 17:
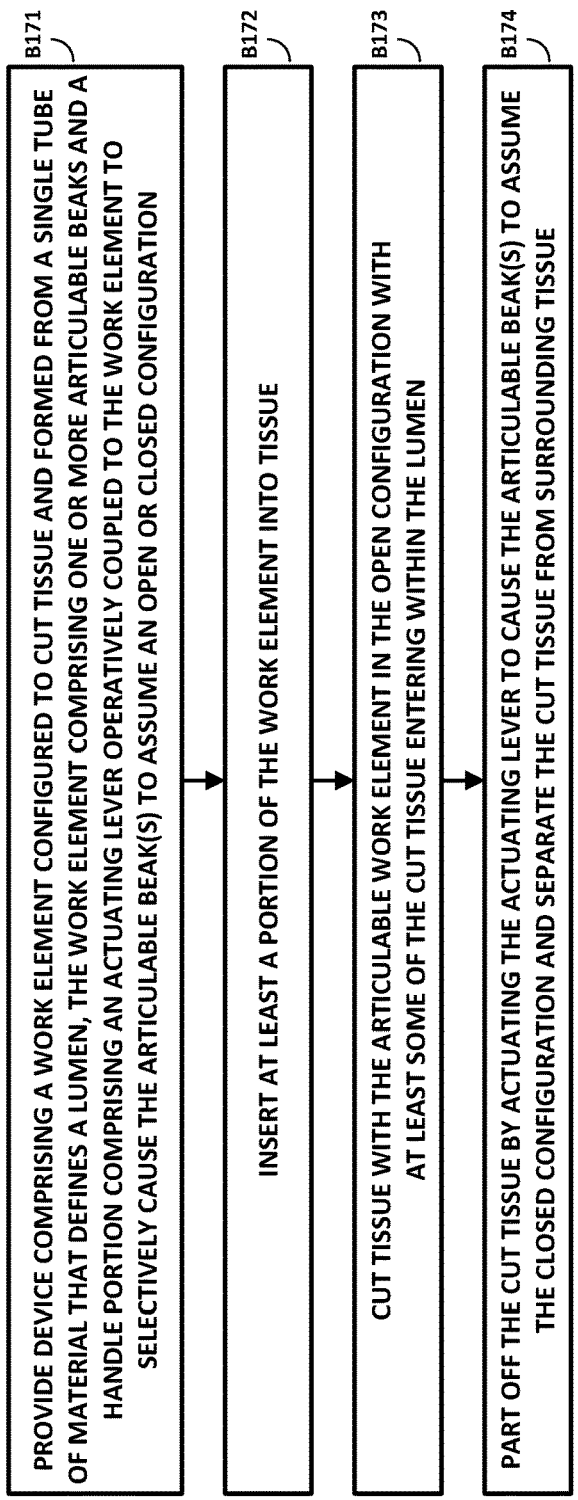
FIG. 17 is a flowchart of a method according to one embodiment.

FIG. 17 is a flowchart of a method according to one embodiment. As shown therein, Block B171 calls for providing a device that comprising a work element configured to cut tissue and that is formed from a single tube of material defining a lumen. The work element comprises at least one (i.e., one or more) articulable beaks and a handle portion comprising an actuating lever operatively coupled to the work element to selectively cause the articulable beak(s) to assume an open or closed configuration. Block B172 calls for inserting at least a portion of the work element into tissue. Tissue may then be cut, as shown at B173, with articulable beak(s) in the open configuration. At least some of the cut tissue enters within the lumen or within the articulable beak(s). Finally, Block B174 calls for parting off the cut tissue by actuating the actuating lever to cause the articulable beak(s) to assume the closed configuration and separate the cut tissue from surrounding tissue.

Figure 18:
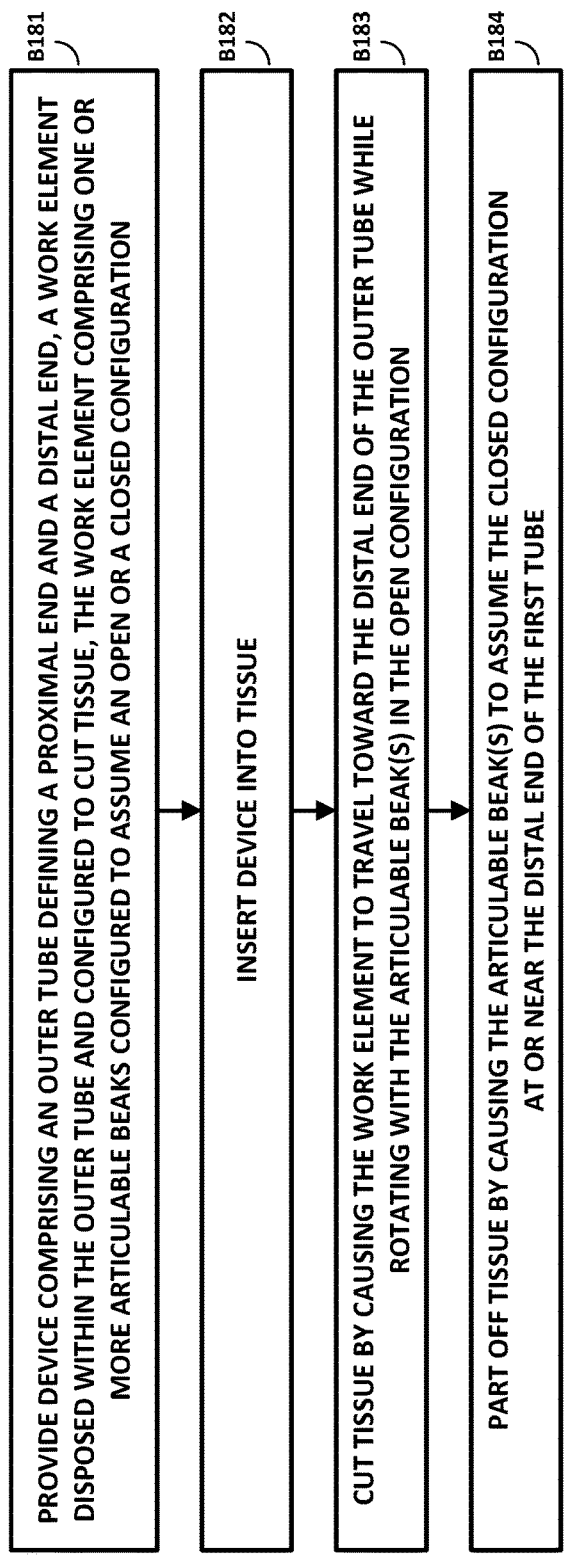
FIG. 18 is a flowchart of a method according to one embodiment.

FIG. 18 is a flowchart of a method according to one embodiment. As shown, B181 calls for providing a device comprising an outer tube defining a proximal end and a distal end and a work element disposed within the outer tube and configured to cut tissue. As shown, the work element comprises at least one (i.e., one or more) articulable beaks configured to assume an open or a closed configuration. Block B182 calls for inserting the provided device into tissue. Tissue may then be cut, as shown at B183, by causing the work element to travel toward the distal end of the outer tube while rotating with the at least one articulable beak in the open configuration. Finally, as shown at B184, tissue may be parted off by causing the articulable beak(s) to assume the closed configuration at or near the distal end of the first tube.

The described embodiments may be formed of or comprise one or more biocompatible materials such as, for example, stainless steel or other biocompatible alloys, and may be made of, comprise or be coated with polymers and/or biopolymer materials as needed to optimize function(s). For example, the cutting elements (such as the constituent elements of a work element 13) may comprise or be made of hardened alloys or carbon fiber or other polymers or plastics, and may be additionally coated with a slippery material or materials to thereby optimize passage through living tissues of a variety of consistencies and frictions. Some of the components may be purposely surface-treated differentially with respect to adjacent components, as may be inferred herein in reference to a transporting tubular and storage component (not shown). The various internal or external components may be made of any suitable, commercially available materials such as nylons, polymers such as moldable plastics, and others. The handle may be configured in such a way as to make it easily adaptable to one of any number of existing guiding platforms, such as stereotactic table stages. The materials used in the present material delivery or removal device may also be carefully selected from a Ferro-magnetic standpoint, such that the present material delivery or removal device maintains compatibility with magnetic resonance imaging (MRI) equipment that is commonly used for material delivery or removal procedures. Vacuum/delivery assembly components may comprise commercially available vacuum pumps, syringes and tubing for connecting to the present material delivery or removal device, along with readily available reed valves for switching between suction and emptying of materials such as fluids which may be suctioned by vacuum components. The fluids collected by the embodiments of the present device in this manner may then be ejected into an additional external, yet portable, liquid storage vessel connected to the tubing of the present device, for safe keeping and laboratory cellular analysis.

While certain embodiments of the disclosure have been described, these embodiments have been presented by way of example only, and are not intended to limit the scope of the disclosure. Indeed, the novel methods, devices and systems described herein may be embodied in a variety of other forms. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures may differ from those shown in the figures. Depending on the embodiment, certain steps described in the example above may be removed, and others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

What is claimed is:

1. A method, comprising:
providing a device comprising an outer tube that defines a spiral slot extending at least partway between a proximal end and a distal end of the outer tube; a work element configured to cut tissue, the work element being formed of a single tube of material that defines a lumen, the work element being disposed within the outer tube; a rivet attached to the work element and engaged within the spiral slot, at least one articulable beak and a handle portion comprising an actuating lever operatively coupled to the work element to selectively cause the at least one articulable beak to assume an open or closed configuration;
inserting at least a portion of the work element into tissue;
actuating the lever to cause the work element to move such that the rivet travels in a distal direction along a spiral path defined by the spiral slot while cutting tissue with the at least one articulable beak in the open configuration, at least some of the cut tissue entering within the lumen; and
continuing to actuate the lever to cause the work element to continue to move such that the rivet travels further in the distal direction along the spiral path while parting off the cut tissue by causing the at least one articulable beak to assume the closed configuration and separate the cut tissue from surrounding tissue.

2. The method of claim 1, wherein actuating the lever further causes the rivet travelling along the spiral path to impart a twist on the work element as the at least one articulable beak is caused to assume the closed configuration.

3. The method of claim 2, wherein the twisting motion is imparted as the cut tissue is being parted off.

4. The method of claim 2, further comprising manually controlling an amount of the twisting motion imparted on the work element.

5. The method of claim 1, further comprising, after inserting, advancing the work element toward the tissue to be cut and coring tissue along the way with the at least one articulable beak in the open configuration.

6. The method of claim 1, further comprising, after inserting, advancing the work element toward the tissue to be cut by dissecting tissue along the way with the at least one articulable beak in the closed configuration.

7. The method of claim 1, further comprising delivering a material to the tissue through the work element.

8. The method of claim 1, wherein at least cutting and parting off is carried out under visualization.

9. A device, comprising:
an outer tube defining a proximal end, a distal end and a spiral slot extending at least partway between the proximal and distal ends;
a work element configured to cut tissue and comprising at least one articulable beak configured to assume an open or a closed configuration, the work element being disposed within the outer tube;
a rivet coupled to the work element and engaged within the spiral slot;
an actuation assembly configured to cause the rivet element coupled to the work element to travel along a spiral path defined by the spiral slot, entraining the work element to move toward the distal end of the outer tube while rotating with the at least one beak in the open configuration and to cause the at least one articulable beak to assume the closed configuration at or near the distal end of the outer tube.

10. The device of claim 9, wherein the at least one articulable beak is configured to part-off tissue upon assuming the closed configuration.

11. The device of claim 9, wherein the work element comprises a first articulable beak and a second articulable beak and wherein the closed configuration in one in which at least one of the first and second articulable beaks close against the other one of the first and second articulable beaks.

12. The device of claim 9, wherein the distal end of the tube comprises a trough-shaped portion and wherein the at least one articulable beak is configured to press against the trough-shaped portion as it assumes the closed configuration.

13. The device of claim 9, wherein further comprising at least one tendon coupled to the at least one articulable beak, the at least one tendon causing the at least first articulable beak to close when the work element is at or near the distal end of the outer tube.

14. The device of claim 9, wherein the work element is formed of a single tube of material that comprises cuts from which material is removed to form the at least one articulable beak.

15. A method, comprising:
providing device comprising:
an outer tube comprising a spiral slot defined therein and defining a proximal end and a distal end;
a work element disposed within the outer tube and configured to cut tissue, the work element comprising at least one articulable beak configured to assume an open or a closed configuration; and
a rivet element that is coupled to the work element and engaged within the spiral slot defined in the outer tube;
inserting the provided device into tissue; and
moving the rivet along a spiral path defined by the spiral slot to:
entrain the work element in both rotation and translation;
cut tissue by causing the work element to travel toward the distal end of the outer tube while rotating with the at least one articulable beak in the open configuration; and part off tissue by causing the at least one articulable beak to assume the closed configuration at or near the distal end of the first tube.

16. The method of claim 15, wherein providing is carried out with the work element comprises a first articulable beak and a second articulable beak and wherein parting off is carried out with at least one of the first and second articulable beaks closing against the other one of the first and second articulable beaks.

17. The method of claim 15, wherein providing is carried out with the distal end of the tube comprising a trough-shaped portion and with the at least one articulable beak pressing against the trough-shaped portion as it assumes the closed configuration.

18. The method of claim 15, wherein providing is carried out with the device further comprising at least one tendon coupled to the at least one articulable beak, the at least one tendon causing the at least first articulable beak to close when the work element is at or near the distal end of the outer tube.

* * * * *